United States Patent
Kuyava

(10) Patent No.: US 8,114,011 B2
(45) Date of Patent: Feb. 14, 2012

(54) CORRUGATED INFLATABLE PENILE PROSTHESIS CYLINDER

(75) Inventor: Charles C. Kuyava, Eden Prairie, MN (US)

(73) Assignee: AMS Research Corporation, Minnetonka, MN (US)

( * ) Notice: Subject to any disclaimer, the term of this patent is extended or adjusted under 35 U.S.C. 154(b) by 466 days.

(21) Appl. No.: 12/256,598

(22) Filed: Oct. 23, 2008

(65) Prior Publication Data

US 2009/0105530 A1    Apr. 23, 2009

Related U.S. Application Data

(60) Provisional application No. 60/981,888, filed on Oct. 23, 2007.

(51) Int. Cl.
*A61F 5/00* (2006.01)

(52) U.S. Cl. ......................................................... 600/40

(58) Field of Classification Search .............. 600/38–41; 128/897–899
See application file for complete search history.

(56) References Cited

U.S. PATENT DOCUMENTS

| | | | |
|---|---|---|---|
| 3,832,996 A | 9/1974 | Kainberz | |
| 3,853,122 A | 12/1974 | Strauch et al. | |
| 3,893,456 A | 7/1975 | Small et al. | |
| 3,954,102 A | 5/1976 | Buuck | |
| 3,987,789 A | 10/1976 | Timm et al. | |
| 3,991,752 A | 11/1976 | Gerow | |
| 4,009,711 A | 3/1977 | Uson | |
| 4,066,073 A | 1/1978 | Finney et al. | |
| 4,151,840 A | 5/1979 | Barrington | |
| 4,151,841 A | 5/1979 | Barrington | |
| 4,177,805 A | 12/1979 | Tudoriu | |
| 4,187,839 A | 2/1980 | Nuwayser et al. | |
| 4,201,202 A | 5/1980 | Finney et al. | |
| 4,204,530 A | 5/1980 | Finney | |
| 4,222,377 A | 9/1980 | Burton | |
| 4,224,934 A | 9/1980 | Scott et al. | |
| 4,235,227 A | 11/1980 | Yamanaka | |
| 4,244,370 A | 1/1981 | Furlow et al. | |
| 4,267,829 A | 5/1981 | Burton et al. | |
| 4,318,396 A | 3/1982 | Finney | |
| 4,342,308 A | 8/1982 | Trick | |

(Continued)

FOREIGN PATENT DOCUMENTS

EP    0051420    5/1982

(Continued)

OTHER PUBLICATIONS

Definition of Corrugation, printed from www.Dictionary.com, Aug. 26, 2011, 1 page.*

(Continued)

*Primary Examiner* — Samuel Gilbert
(74) *Attorney, Agent, or Firm* — Westman, Champlin & Kelly, P.A.

(57) ABSTRACT

An inflatable penile prosthesis of the present invention includes a cylinder that has an external wall that defines a pressure chamber. That external wall preferably incorporates a number of corrugations that extend in a longitudinal direction of the cylinder. In a preferred embodiment, the external wall of the cylinder is formed of a polyurethane or of a material having a modulus of elasticity greater than that of silicone. The corrugations enable the cylinder to move from a small, deflated diameter to a much greater diameter in the inflated state.

6 Claims, 2 Drawing Sheets

U.S. PATENT DOCUMENTS

| | | | |
|---|---|---|---|
| 4,345,339 A | 8/1982 | Muller et al. | |
| 4,353,360 A | 10/1982 | Finney et al. | |
| 4,360,010 A | 11/1982 | Finney | |
| 4,364,379 A | 12/1982 | Finney | |
| 4,369,771 A | 1/1983 | Trick | |
| 4,378,792 A | 4/1983 | Finney | |
| 4,383,525 A | 5/1983 | Scott et al. | |
| 4,392,562 A | 7/1983 | Burton et al. | |
| 4,399,811 A | 8/1983 | Finney et al. | |
| 4,399,812 A | 8/1983 | Whitehead | |
| 4,404,968 A | 9/1983 | Evans, Sr. | |
| 4,407,278 A | 10/1983 | Burton et al. | |
| 4,411,260 A | 10/1983 | Koss | |
| 4,411,261 A | 10/1983 | Finney | |
| 4,412,530 A | 11/1983 | Burton | |
| 4,424,807 A * | 1/1984 | Evans, Sr. | 600/40 |
| 4,441,491 A | 4/1984 | Evans, Sr. | |
| 4,449,520 A | 5/1984 | Palomar | |
| 4,457,335 A | 7/1984 | Trick | |
| 4,483,331 A | 11/1984 | Trick | |
| 4,517,967 A | 5/1985 | Timm et al. | |
| 4,522,198 A | 6/1985 | Timm et al. | |
| 4,523,584 A * | 6/1985 | Yachia et al. | 600/38 |
| 4,532,920 A * | 8/1985 | Finney | 600/40 |
| 4,541,420 A | 9/1985 | Timm et al. | |
| 4,545,081 A | 10/1985 | Nestor et al. | |
| 4,550,719 A | 11/1985 | Finney et al. | |
| 4,550,720 A | 11/1985 | Trick | |
| 4,558,693 A | 12/1985 | Lash et al. | |
| 4,559,931 A | 12/1985 | Fischell | |
| 4,566,446 A | 1/1986 | Fogarty | |
| 4,572,168 A | 2/1986 | Fischell | |
| 4,574,792 A | 3/1986 | Trick | |
| 4,590,927 A | 5/1986 | Porter et al. | |
| 4,594,998 A | 6/1986 | Porter et al. | |
| 4,596,242 A | 6/1986 | Fischell | |
| 4,602,625 A * | 7/1986 | Yachia et al. | 600/40 |
| 4,604,994 A | 8/1986 | Sealfon | |
| 4,611,584 A | 9/1986 | Finney | |
| 4,619,251 A | 10/1986 | Helms et al. | |
| 4,622,958 A | 11/1986 | Finney | |
| 4,651,721 A | 3/1987 | Mikulich et al. | |
| 4,653,485 A | 3/1987 | Fischell | |
| 4,664,100 A | 5/1987 | Rudloff | |
| 4,665,902 A | 5/1987 | Goff et al. | |
| 4,665,903 A | 5/1987 | Whitehead | |
| 4,666,428 A | 5/1987 | Mattioli et al. | |
| 4,669,456 A | 6/1987 | Masters | |
| 4,671,261 A * | 6/1987 | Fischell | 600/40 |
| 4,682,583 A | 7/1987 | Burton et al. | |
| 4,682,589 A | 7/1987 | Finney | |
| 4,693,719 A | 9/1987 | Franko et al. | |
| 4,699,128 A | 10/1987 | Hemmeter | |
| 4,718,410 A | 1/1988 | Hakky | |
| 4,724,830 A | 2/1988 | Fischell | |
| 4,726,360 A | 2/1988 | Trick et al. | |
| 4,730,607 A | 3/1988 | Fischell | |
| 4,766,889 A | 8/1988 | Trick et al. | |
| 4,773,403 A | 9/1988 | Daly | |
| 4,782,826 A | 11/1988 | Fogarty | |
| 4,790,298 A | 12/1988 | Trick | |
| 4,791,917 A | 12/1988 | Finney | |
| 4,807,608 A | 2/1989 | Levius | |
| 4,829,990 A | 5/1989 | Thuroff et al. | |
| 4,881,530 A | 11/1989 | Frick | |
| 4,881,531 A | 11/1989 | Timm et al. | |
| 4,895,139 A | 1/1990 | Hauschild et al. | |
| 4,899,737 A | 2/1990 | Lazarian | |
| 4,917,110 A | 4/1990 | Trick | |
| 4,988,357 A | 1/1991 | Koss | |
| 5,010,882 A | 4/1991 | Polyak et al. | |
| 5,048,511 A | 9/1991 | Hauschild et al. | |
| 5,050,592 A | 9/1991 | Olmedo | |
| 5,062,416 A | 11/1991 | Stucks | |
| 5,062,417 A | 11/1991 | Cowen | |
| 5,063,914 A | 11/1991 | Cowen | |
| 5,067,485 A | 11/1991 | Cowen | |
| 5,101,813 A | 4/1992 | Trick | |
| 5,112,295 A | 5/1992 | Zinner et al. | |
| 5,114,398 A | 5/1992 | Trick et al. | |
| 5,129,880 A | 7/1992 | Grundei | |
| 5,141,509 A | 8/1992 | Burton et al. | |
| 5,167,611 A | 12/1992 | Cowan | |
| 5,171,272 A | 12/1992 | Levius | |
| 5,176,708 A | 1/1993 | Frey et al. | |
| 5,250,020 A | 10/1993 | Bley | |
| 5,263,981 A | 11/1993 | Polyak et al. | |
| 5,283,390 A | 2/1994 | Hubis et al. | |
| 5,344,388 A | 9/1994 | Maxwell et al. | |
| 5,433,694 A | 7/1995 | Lim | |
| 5,445,594 A | 8/1995 | Elist | |
| 5,509,891 A | 4/1996 | DeRidder | |
| 5,512,033 A | 4/1996 | Westrum, Jr. et al. | |
| 5,553,379 A | 9/1996 | Westrum, Jr. et al. | |
| 5,669,870 A * | 9/1997 | Elist | 600/40 |
| 5,704,895 A | 1/1998 | Scott et al. | |
| 5,851,176 A | 12/1998 | Willard | |
| 5,895,424 A | 4/1999 | Steele, Sr. et al. | |
| 5,899,849 A | 5/1999 | Elist | |
| 6,171,233 B1 | 1/2001 | Willard | |
| 6,346,492 B1 | 2/2002 | Koyfman | |
| 6,443,887 B1 | 9/2002 | Derus et al. | |
| 6,533,719 B2 | 3/2003 | Kuyava et al. | |
| 6,558,315 B1 | 5/2003 | Kuyava | |
| 6,579,230 B2 | 6/2003 | Yachia et al. | |
| 6,600,108 B1 | 7/2003 | Mydur et al. | |
| 6,723,042 B2 | 4/2004 | Almli et al. | |
| 6,730,017 B2 | 5/2004 | Henkel et al. | |
| 6,733,527 B2 | 5/2004 | Koyfman | |
| 6,929,599 B2 | 8/2005 | Westrum | |
| 6,935,847 B2 | 8/2005 | Kuyava et al. | |
| 6,991,601 B2 | 1/2006 | Kuyava et al. | |
| 7,066,877 B2 | 6/2006 | Kuyava | |
| 7,066,878 B2 | 6/2006 | Francois | |
| 7,169,103 B2 | 1/2007 | Ling et al. | |
| 7,244,227 B2 | 7/2007 | Morningstar | |
| 7,250,026 B2 | 7/2007 | Kuyava | |
| 7,350,538 B2 | 4/2008 | Kuyava et al. | |
| 7,390,296 B2 | 6/2008 | Hans | |
| 7,438,682 B2 | 10/2008 | Henkel et al. | |
| 7,491,164 B2 | 2/2009 | Choi et al. | |
| 7,637,861 B2 | 12/2009 | Kuyava et al. | |
| 2002/0033564 A1 | 3/2002 | Koyfman | |
| 2002/0082473 A1 | 6/2002 | Henkel et al. | |
| 2002/0082709 A1 | 6/2002 | Almli et al. | |
| 2002/0091302 A1 | 7/2002 | Kuyava et al. | |
| 2003/0028076 A1 | 2/2003 | Kuyava et al. | |
| 2004/0220447 A1 | 11/2004 | Morningstar | |
| 2005/0014993 A1 | 1/2005 | Mische | |
| 2006/0235267 A1 | 10/2006 | George et al. | |
| 2008/0103353 A1 | 5/2008 | Jahns et al. | |
| 2008/0114202 A1 | 5/2008 | Kuyava et al. | |
| 2009/0105818 A1 | 4/2009 | George et al. | |
| 2009/0124851 A1 | 5/2009 | Kuyava et al. | |
| 2009/0287042 A1 | 11/2009 | Almli et al. | |

FOREIGN PATENT DOCUMENTS

| | | |
|---|---|---|
| EP | 0065853 | 12/1982 |
| EP | 0137752 B1 | 8/1989 |
| EP | 0774935 B1 | 7/1995 |
| EP | 0682923 | 11/1995 |
| EP | 0925764 | 6/1999 |
| GB | 2151484 A | 7/1985 |
| GB | 2160777 | 1/1986 |
| GB | 2192546 | 1/1988 |
| WO | WO8000302 | 3/1980 |
| WO | WO8500513 | 2/1985 |
| WO | 8601398 A1 | 3/1986 |
| WO | WO9203107 | 3/1992 |
| WO | WO9404095 | 3/1994 |
| WO | 9604865 A1 | 2/1996 |
| WO | WO02/051339 | 7/2002 |

OTHER PUBLICATIONS

Abouassaly, R. et al, "Antibiotic-coated medical devices: with an emphasis on inflatable penile prosthesis", Asian J Androl. Sep. 2004; 6: 249-57.

Agrawal, V. et al. "An audit of implanted penile prostheses in the UK", BJU International 98, 293-295 (2006).

Akin-Olugbade, O. et al, "Determinants of Patient Satisfaction Following Penile Prosthesis Surgery", J Sex Med 2006; 3: 743-48.

Al-Najar, A., et al, "Should being aged over 70 years hinder penile prosthesis implantation?", BJU International 2009 1-4.

AMS 700 CX Penile Prosthesis (Brochure) 2 pages 1999.

AMS 700 Inflatable Penile Prosthesis Product Line 45 pages (1992).

AMS (Brochure) 700 Series Tactiel (Pump 2 pages) 2004.

AMS (Brochure) Ultrex/Ultrex Plus (10 Pages)(1998).

AMS Ambicor Penile Prosthesis (Brochure) 1996.

Merino, G. Atienza, "Penile Prosthesis for the treatment of erectile dysfunction" Actas Urol Esp. 2006; 30(2): 159-69.

Bella, A. et al, "Initial experience with 50 patients using the new AMS 700 with MS Pump Series inflatable penile prosthesis" Poster # 44 J Sex Med, Jan. 2008;5(suppl 1) p. 20.

Candela, J. et al "Three-piece inflatable penile prosthesis implantatoin: . . . " J La State Med Soc 148:296-301 (1996).

Daitch, J. et al, "Long-Term Mechanical Reliability of AMS 700 Series Inflatable Penile Prostheses: Comparison . . . " J. Urol. 158: 1400-1402; Oct. 1997.

Delk, J. "Early Experience with the American Medical Systems New Tactile Pump: Results of a Multicenter Study" J Sex med 2005; 2: 266-271.

Deuk Choi, Y. et al. "Mechanical Reliability of the AMS 700CXM Inflatable Penile Prosthesis for the Treatment of Male Erectile Dysfunction" J. Urol 168, 822-824, Mar. 2001.

Deveci, S. et al "Penile Length Alterations following Penile Prosthesis Surgery" Europan Urol. 51 (2007) 1128-31.

Durazi,. M, et al. "Penile Prosthesis Implantation for Treatment of Postpriapism Erectile Dysfunctoin" Urol. J. 5(2) (2008) 115-19.

Eid, J. "What is new for inflatable penile prostheses?" Curr Opin. Urol 19:582-588 (2009).

Gefen, A. "Stresses in the normal and diabetic human penis following implantation of an inflatable prosthesis." Med. Biol. Eng. Comput., 1999, 37, 625-31.

Garber, B. "Inflatable penile prostheses for the treatment of erectile dysfunction." Exper Rev. Med. Devices 2(3), 341-50 (2005).

Gefen, A et al. "A biomechanical model of Peyronie's disease" J. Biomech.33 (2000) 1739-44.

Gefen, A et al. "Optimization of Design and Surgical Positioning of Inflatable Penile Prostheses" Annals of Biomed. Eng. 28 (2000) 619-28.

Henry, G., et al "Revision Washout Decreases Implant Capsule Tissue Culture Positivity: A Multicenter Study" J Urol. vol. 179, 186-190, Jan. 2008.

Henry, G "Historical Review of Penile Prosthesis Design and Surgical Techniques: Part 1 of a Three-Part Review Series on Penile Prosthetic Surgery" J Sex Med 2009;6:675-681.

Henry, G "Advances in Penile Prosthesis Design", Current Sexual Health Reports 2007, 4:15-19.

Henry, G. "Updates in Inflatable Penile Prostheses" Urol Clin N. Am 34 (2007) 535-547.

Hoebeke, P., et al. "Erectile Implants in Female-to-Male Transsexuals:Our Experience in 129 Patients" Eur Urol (2009), doi:10. 1016/j.eururo.2009.03.013.

InhibiZone Antibiotic Surface Treatment, (AMS Brochure) 4pgs 2001.

Kadioglu, A. et al. "Surgical Treatment of Peyronie's Disease: A Critical Analysis" european urology 50 (2006) 235-248.

Kava B et al "Efficacy and Patient Satisfaction Associated with Penile Prosthesis Revision Surgery" J Sex Med 2007;4:509-518.

Lazarou, S., et al, "Technical Advances in Penile Prostheses" J Long-Term Effects of Med. Imp. 16(3):235-247 (2006).

Leriche, A., Long-term outcome of forearm flee-lap phalloplasty in the treatment of transsexualism: BJU International 101: 1297-1300 2008.

Levine, L et al, "Mechanical Reliability and Safety of, and Patient Satisfaction With the Ambicor Inflatable Penile Prosthesis: Results of a 2 Center Study" J Urol vol. 166, 932-937, Sep. 2001.

Lumen, N. "Phalloplasty: A Valuable Treatment for Males with Penile Insufficiency", Urology 71 (2), 2008 272-276.

Lux, M. et al. "Outcomes and Satisfaction Rates for the Redesigned 2-Piece Penile Prosthesis" J Urol. vol. 177, 262-266, Jan. 2007.

Mentor New from Mentor Urology Alpha I Narrow-Base (Brochure) 2pgs 1996.

Mentor Alpha I Inflatable Penile Prosthesis (Brochure) 2 pgs. Jul. 1996.

Mentor Surgical Protocol Alpha I Inflatable Penile Prosthesis 17pgs May 1998.

Mentor Patient Guide for Alpha I Inflatable Penile Implant (Brochure) 2pgs 1997.

Montague, D., "Penile Prosthesis Implantation for End-Stage Erectile Dysfunction After Radical Prostatectomy" Reviews in Urol. vol. 7 Suppl. 2 2O05 S51-S57.

Mulcahy, J. "Distal Corporoplasty for Lateral Extrusion of Penile Prosthesis Cylinders" J. Urol. vol. 161, 193-195 Jan. 1999.

Murphy, AM., et al. "Failure of the Ambicors inflatable penile prosthesis to deflate" International Journal of Impotence Research (2005) 17, 291-292.

Nahdrstad, BC "Informed consent for penile prosthesis", International Journal of Impotence Research (2009) 21, 37-50.

Natali, A "Penile Implantation in Europe: Successes and Complications with 253 Implants in Italy and Germany" J Sex Med 2008;5:1503-1512.

"Parylene Micro Coating" AMS Brochure, 4 pgs. 2000.

Sadeghi-Nejad, H. "Penile Prosthesis Surgery: A Review of Prosthetic Devices and Associated Complications" J Sex Med 2007;4:296-309.

Scarzella, IG,. et al. "Use of Amibcor Penile Prosthesis in Peyronie's Disease and as Replacement for Malfunctioning AMS 700 Devices", J Sex Med 2004; Suppl. 1.

Simmons, M. et al "Penile prosthesis implantation: past, present and future", International Journal of Impotence Research (2008) 20, 437-444.

Ultrex Plus Penile Prosthesis (AMS Advertisement) 1 pg (1992).

Wang, Shyh-Jen, et al "Hardness evaluation of penile prostheses" Internationa Journal of Urology (2006) 13, 569-572.

Mentor Surgical Protocol Alpha I Inflatable Penile Prosthesis 15pgs 1998.

Mentor Urology Products, (Brochure), Mentor, 20 pages (1998).

Hellstrom, WJG, "Three-piece inflatable penile prosthesis components (surgical pearls on reservoirs, pumps, and rear-tip extenders)" International Journal of Impotence Research (2003) 15, Suppl 5, S136-S138.

Kim, Sae-Chui, "Mechanical Reliability of AMS Hydraulic Penile Prostheses" J. of Korean Med. Sci. 10(6); 422-425, Dec. 1995.

Mooreville, M. et al "Implantation of Inflatable Penile Prosthesis in Patients With Severe Corporeal Fibrosis: Introduction of a New Penile Cavernotome" J. Urol 162, 2054-2057, Dec. 1999.

Montague, DK., "Early Experience with the Controlled Girth and Length Expanding Cylinder of the American Medical Systems Ultrex Penile Prosthesis", J. Urol. 148; 1444-1446, Nov. 1992.

Montague, DK "Cylinder Sizing: less is more" International Journal of Impotence Research (2003) 15, Suppl 5, S132-S133.

Montague, DK et al. "AMS 3-Piece Inflatable Penile Prosthesis Implantation in Men with Peyronie's Disease: Comparison of Cx and Ultrex Cylinders" J. Urol. 156, 1633-1635, Nov. 1996.

Montague, DK et al, "Penile Prosthesis Infections" International Journal of Impotence Research (2001) 13, 326-328.

Malloy, T., et al.,"Improved Mechanical Survival with Revised Model Inflatable Penile Prosthesis Using Rear-Tip Extenders", J Urol. 128 Sep. 1982 489-491.

Chang, Yao-Jen, et al "Penile Prosthesis Implantation" eMedicine http://www.emedicine.com/med/topic3047.htm 19 pages (2003).

Gregory, J., et al., "The Inflatable Penile Prosthesis: Failure of the Rear Tip Extender in Reducing the Incidence of Cylinder Leakage" J Urol. vol. 131 668-669 (1984).

Joseph, D., et al., "Bilateral Disloctin of Rear Tip Extenders from the Inflatable Penile Prosthesis" J Urol vol. 128, Dec. 1982 1317-1318.

Acu-Form Penile Prosthesis, Mentor, 1 page Aug. 1997.

Agrawal, Wineet et al., An Audit of Implanted Penile Prosthesis in the UK, BJU International pp. 393-395 (2006).

Akand, Murat, Mechanical Failure with Malleable Penile Prosthesis, J. Urol. 70:1007 ell-1007 e12 (2007).

AMS Malleable 600 TM American Medical Systems Publication 30915, 1983.
Anafarta, Kadri, Clinical Experience with Inflatable and Malleable Penile Implants in 104 Patients, Urol. Int. 56:100-104 (1996).
Burns-Cox, N., Fifteen Years Experience of Penile Prosthesis Insertion, International J. Impotence Res. (1997) 9, 211-216.
Chiang, Han-Sun, 10 Years Experience with Penile Prosthesis Implantation in Taiwanese Patients, J. Urol. vol. 163:476-480 (2000).
Choi, Hyung Ki, Ten Years of Experience with Various Penile Prosthesis in Korean, Yasei Medical J. vol. 35, No. 2 (1994) 209-217.
Dorflinger T, Bruskewitz R, AMS Malleable Penile Prosthesis, Urology, Dec. 1986; 28(6):480-5.
Fathy, Ahmad, Experience with Tube (Promedon_Malleable Penile Implant, Urol. Int. 2007; 79:244-247.
Ferguson, Kenneth, Prospective Long-Term Results and Quality-of-Life-Assessment After Dura-II Penile Prosthesis Placement, Urol. 61(2) 437-441 (2003).
Fogarty, JD, Cutaneous Temperature Measurements in Men with Penile Prosthesis: A Comparison Study, Int. J. of Impotence Res. (2005) 17,506-509.
Jonas U. Silicone-Silver Penis Prosthesis (Jonas-Eska), Long-Term Reconstruction. J. Urol. Sep. 1998; 160(3 Pt 2):1164-8.
Kardar, A.H., An Unusual Complication of Penile Prosthesis Following Urethroplasty, Scand. J. Urol. Nephrol. 36: 89-90, 2002.
Kaufman, JJ, Raz S. Use of Implantable Prostheses for the Treatment of Urinary Incontinence and Impotence, Am J Surg. Aug. 1975; 130(2):244-50.
Khoudary, Kevin, Design Considerations in Penile Prostheses: The American Medical Systems Product Line, J. Long-Term Effects of Medical Implants, 7(1):55-64 (1997).
Krauss, Dennis J., Use of the Malleable Penile Prosthesis in the Treatment of Erectile Dysfunction: A Prospective Study of Postoperative . . . , J. Urol. vol. 142: 988-991 (1989).
Montague, Drogo, Surgical Approaches for Penile Prostheses Implantation: Penoscrotal VS Infrapubic, International J. Impotence Res. (2003) 15, Suppl. 5, S134-S135.
Morey, Allen et al., Immediate Insertion of a Semirigid Penile Prosthesis for Refractory Ischemic Priapism, Military Medicine, 172, 11:1211, 2007.
Mulcahy, John, Another Look at the Role of Penile Prostheses in the Management of Impotence, Urology Annual 11, pp. 169-185 (1997).
Parulkar, B.G., Revision Surgery for Penile Implants, Int. J. Impotence res. (1994) 6, 17-23.
Pearman, Ro, Insertion of a Silastic Penile Prosthesis for the Treatment of Organic Sexual Impotence. J. Urol. May 1972; 107(5):802-6.
Randrup, Eduardo, Penile Implant Surgery: Rear Tip Extender That Stays Behind, Urology 1992 34, 1 p. 87.
Rhee, Eugene, Technique for Concomitant Implantation of the Penile Prosthesis with the Male Sling. J. Urol. 173:925-927 (2006).
Salama, Nadar, Satisfaction with the Malleable Penile Prosthesis Among Couples from the Middle East: Is it Different . . . , Int. J. Impotence Res. 16:175-180 (2004).

Smith, Christopher, Management of Impending Penile Prosthesis Erosion with a Polytetrafluoroethylene Distal Wind Sock Graft, J. Urol. vol. 160: 2037-2040, (1998).
Maul, Judd, Experience with the AMS 600 Malleable Penile Prosthesis, J. Urol. 135:929-931 (1986).
Mentor Urology Products, 18 pages, May (1998).
Merino, G. Atienza, Penile Prosthesis for the Treatment of Erectile Dysfunction, Actas Urol. Esp. 2006: 30(2): 159-169.
Minervini, Andrea, Outcome of Penile Prosthesis Implantation for Treating Erectile Dysfunction: Experience with 504 Procedures, BJU International 97:129-133, (2005).
Montague, Drogo, Clinical Guidelines Panel on Erectile Dysfunction: Summary Report on the Treatment of Organic Erectile Dysfunction, J. Urol. 156:2007-2011 (1996).
Montague, Drogo, Contemporary Aspects of Penile Prosthesis Implantation, Urol. Int. 2003: 70:141-146.
Montague, Drogo, Current Status of Penile Prosthesis Implantation, Urology Reports 2000, 1: 291-296.
Montague, Drogo, Experience with Semirigid Rod and Inflatable Penile Prostheses, J. Urol. 129:967-968, 1983.
Montague, Drogo, Penile Prosthesis Implantation, 712-719, 1994.
Montague, Drogo, Penile Prosthesis Implantation for End-Stage Erectile Dysfunction After Radical Prostatectomy, Reviews in Urol. vol. 7 Suppl. 2 S51-S57, 2005.
Stein, Avi et al., Malleable Penile Prosthesis Removal Leaving Behind the Rear Tip Extenders: A Clinical Presentation, Urol. Int. 50:119-120 (1993).
Surgical Protocol, Mentor 5 pages Sep. 1997.
The AMS Hydroflex Self-Contained Penile Prosthesis, American Medical Systems Publication 50513 (1985).
YOO JJ, Lee I, Atala A. Cartilage Rods as a Potential Material for Penile Reconstruction, J. Urol. Sep. 1998; 160(3 Pt 2): 1164-8; discussion 1178.
Zerman, Dirk-Henrik, et al., Penile Prosthetic Surgery in Neurologically Impaired Patients: Long-Term Follow-Up, J. Urol. 175; 1041-1044 (2006).
Kimoto, Yasusuke, et al., JSSM Guidelines for Erectile Dysfunction, Int. J. Urol (2008) 15, 564-76.
Natali, Alessandro, et al., Penile Implantation in Europe: Successes and Complications with 253 Implants in Italy and Germany, J Sex. Med. 2008;5: 1503-12.
Montague, DK et al., "Future considerations: advances in the surgical management of erectile dysfunction", International J. Impotence Res. (2000) 12, Suppl 4, S140-S143.
Benson RC Jr., Patterson DE, Barrett DM, Long-term results with the Jonas malleable penile prosthesis. J. Urol. vol. 134, Nov. 1985 pp. 899-901.
Small, Michael, Small-Carrion Penile Prosthesis: A Report on 160 Cases and Review of the Literature. J. Urol. vol. 167, Jun. 2002 pp. 2357-2360.
Mentor Alpha I®, The Results are In, 15 pages (Apr. 1997).

\* cited by examiner

CORRUGATED INFLATABLE PENILE PROSTHESIS CYLINDER

CLAIM TO PRIORITY

The present application claims priority to U.S. provisional patent application No. 60/981,888, filed Oct. 23, 2007, and entitled "Corrugated Inflatable Penile Prosthesis Cylinder." The identified provisional patent application is hereby incorporated by reference in its entirety.

FIELD OF THE INVENTION

The present invention relates to inflatable penile prostheses and, more particularly, relates to the configuration of the outer surface of the cylinders that form a component of the inflatable penile prostheses.

BACKGROUND OF THE INVENTION

One common treatment for male erectile dysfunction includes the implantation of a penile implant device. One type of penile implant device includes a pair of cylindrical prostheses that are implanted into the corpus cavernsae of the penis. Typically, the cylindrical prostheses or cylinders are inflatable and are connected to a fluid-filled reservoir through a pump and valve assembly. With one such type of system, one tube extends from each of the two cylindrical prostheses and connects to the pump, and one tube connects the pump to the reservoir. The pump is typically surgically implanted into the scrotum of the patient and the reservoir is implanted in the abdomen, with the tubes fluidly connecting the components. To activate the penile implant device, the patient actuates the pump using one of a variety of methods that cause fluid to be transferred from the reservoir through the pump and into the cylindrical prostheses. This results in the inflation of the prostheses and produces rigidity for a normal erection. Then, when the patient desires to deflate the prostheses, a valve assembly within the pump is actuated in a manner such that the fluid in the prostheses is released back into the reservoir. This deflation returns the penis to a flaccid state.

It is desirable that in an inflated state, the cylinders of the prosthesis expand to the greatest possible diameter, however, it is also desirable that non-inflated cylinders be of a small diameter for easier surgical implantation. These conflicting desires are addressed by the corrugated penile prosthesis cylinder of the present invention.

SUMMARY OF THE INVENTION

An inflatable penile prosthesis of the present invention includes a cylinder that has an external wall that defines a pressure chamber. That external wall preferably incorporates a number of corrugations that extend in a longitudinal direction of the cylinder. In a preferred embodiment, the external wall of the cylinder is formed of a polyurethane or of a material having a modulus of elasticity greater than that of silicone. The corrugations enable the cylinder to move from a small, deflated diameter to a much greater diameter in the inflated state.

A method of the present invention provides for expanding a penile prosthesis cylinder from a deflated state to an inflated state. The cylinder includes an external wall the defines a pressure chamber. A number of corrugations are formed in the external wall and extend in a longitudinal direction of the cylinder. The method includes the steps of: (1) providing the penile prosthesis cylinder in a deflated state in which first and second interior surfaces of the corrugations are displaced from each other a distance D measured in a radial direction; (2) increasing the pressure within the pressure chamber; and (3) reducing the distance D to a distance D' thereby increasing the circumference and diameter of the cylinder.

DESCRIPTION OF THE PREFERRED EMBODIMENTS

Various types of penile prosthesis are currently available to cure or compensate for impotence, two of which include a non-inflatable, semi-rigid implantable prosthesis and an inflatable, implantable prosthesis. The non-inflatable, semi-rigid prosthesis is implanted within the corpora cavernosa of the penis and provides a generally constant erection. The inflatable prosthesis is also implanted in the corpora cavernosa but is connected to a hydraulic pumping device. The hydraulic pumping device is located within the patient's body and is used to inflate the prosthesis for erection and deflate the prosthesis for flaccidity.

Figure 1:
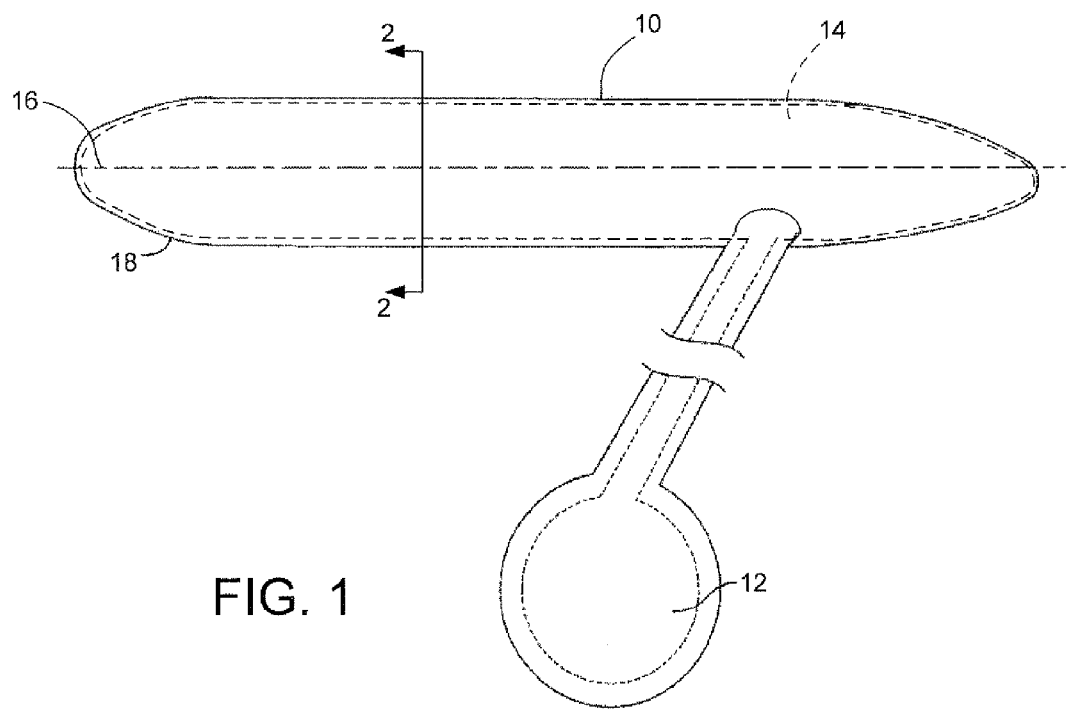
FIG. 1 is a simplified side cross-sectional of an inflatable implantable penile prosthesis.
Figure 2:
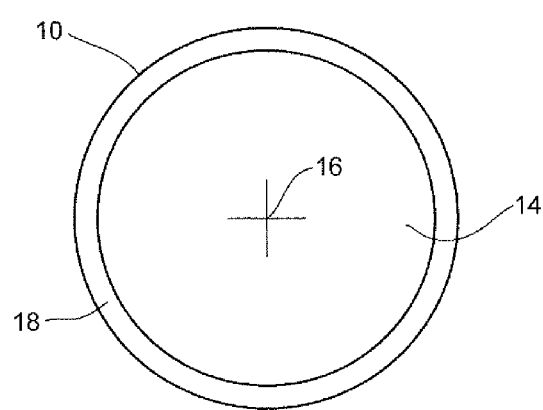
FIG. 2 is a cross section taken along line 2-2 of FIG. 1.

Inflatable, implantable prostheses commonly include two inflatable cylinders: one for each channel of the corpora cavernosa. FIG. 1 is a simplified side cross-sectional view of an exemplary penile prosthesis that includes an inflatable cylinder 10 formed of polyurethane and a pump 12 that is used to inflate or deflate the cylinder by pumping fluid into a chamber 14, in accordance with the prior art. FIG. 2 is a cross-sectional view of the cylinder 10 taken generally along line 2-2 of FIG. 1. The inflation of the chamber 14 results in an expansion of the diameter of the cylinder 10 or an expansion in the radial direction that is perpendicular to the longitudinal axis 16.

The polyurethane material used to form the wall 18 of the cylinder 10 has a much higher modulus of elasticity than silicone elastomers, which are used in inflatable cylinder designs produced by American Medical Systems. Unlike the cylinders that are formed of silicone, the polyurethane cylinder 10 does not require the use of an expansion-constraining sleeve to define the desired shape of the cylinder. Rather, the low modulus of elasticity of the cylinder 10 prevents the undesired bulging of the cylinder and allows it to maintain the desired shape during expansion under normal operating pressures.

However, there are disadvantages to the limited expansion capability of the polyurethane cylinder 10. For instance, in order to provide the desired large inflated state volume for the polyurethane cylinder 10, its deflated (flaccid) diameter must be large. The large diameter of the polyurethane cylinder 10 in its deflated state complicates installation of the cylinder 10 into the corpora cavernosa of the patient. Additionally, the large diameter of the polyurethane cylinder 10 in its deflated state is also uncomfortable for the patient after installation. Finally, the thin walls and the high material stiffness of the polyurethane cylinder 10 also produces very palpable sharp corners at folds in the cylinder 10, making the large deflated state of the cylinder even more uncomfortable for the patient.

Figure 3:
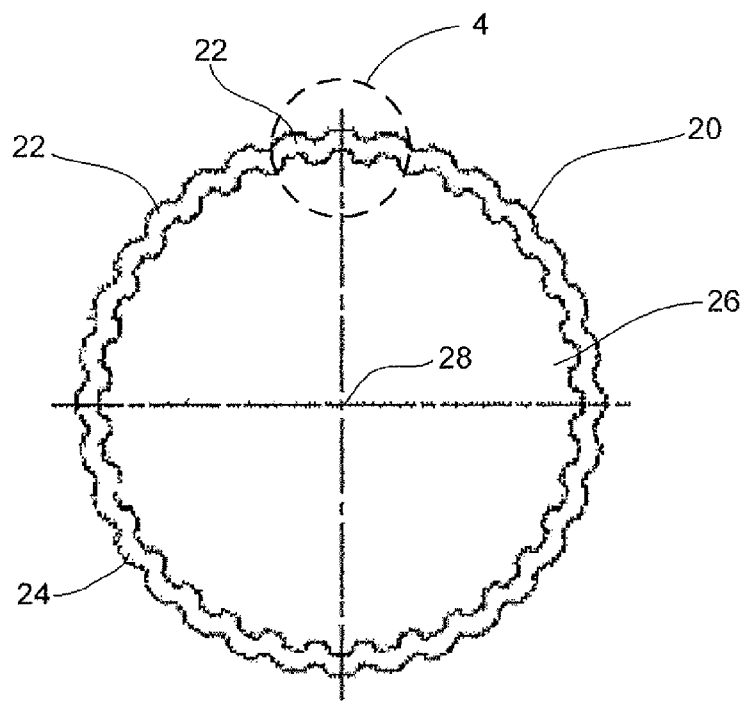
FIG. 3 is a cross section of the prosthesis of the present invention including longitudinal corrugations.

Embodiments of the present invention generally relate to a corrugated inflatable penile prosthesis cylinder 20, a cross-sectional view of which is provided in FIG. 3. The prosthesis cylinder 20 is formed of a material having a relatively high modulus of elasticity as compared to the designs formed of silicone that use an expansion-constraining sleeve. One exemplary material is polyurethane, but other suitable materials can also be used to form the cylinder 20.

Cylinder 20 generally operates as described above with respect to FIG. 1. However, unlike cylinder 10 of the prior art, embodiments of cylinder 20 of the present invention include corrugations 22 formed in an external wall 24 that defines the interior chamber 26. The corrugations 22 run lengthwise or substantially parallel to the longitudinal axis 28. In one embodiment, the corrugations 22 run substantially the entire length of the cylinder 20. However, the corrugations may not necessarily be formed in the tapered ends of the cylinder 20, such as those depicted for cylinder 10 in FIG. 1.

The corrugations 22 can be formed by any suitable method. One exemplary method includes forming the mold used to produce the cylinder 20 with the desired corrugations 22.

Figure 4:
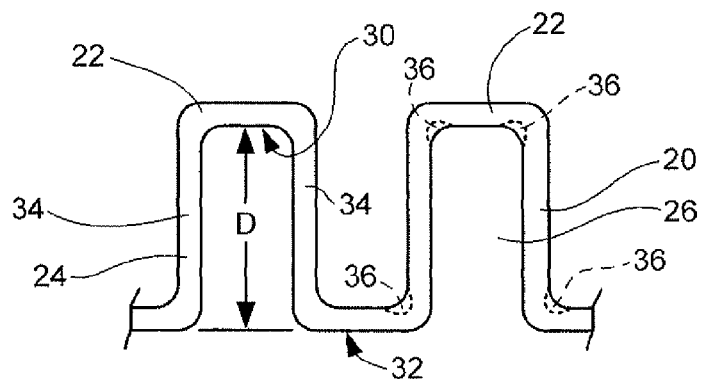
FIG. 4 is a magnified view of a section of FIG. 3 when the prosthesis is in a deflated state.
Figure 5:
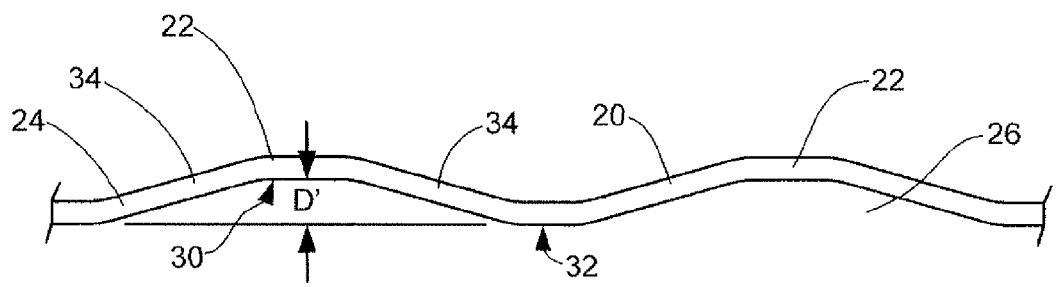
FIG. 5 is a magnified view of a section of FIG. 3 when the prosthesis is in an inflated state.

FIGS. 4 and 5 are magnified views of the external wall 24 of the cylinder 20 approximately within circle 4, when the cylinder 20 is in a deflated state and an inflated state, respectively. The corrugations 22 can take on many different cross-sectional shapes, including the somewhat rectangular shape depicted in FIG. 4. Other exemplary shapes include more rounded or arched corrugations, triangular corrugations, and other cross-sectional shapes.

The corrugations 22 allow cylinder 20 to expand radially (i.e., in a direction that is perpendicular to the longitudinal axis 28) from the deflated state to the inflated state in response to an increase in pressure within the chamber 26. The increase in pressure within the chamber 26 can be the result of pumping fluid into the chamber 26, as described above, or other suitable method.

The deflated state of the cylinder 20 (FIG. 4) is proximate to a quiescent state of the cylinder 20, to which the cylinder 20 will naturally return from an inflated state (FIG. 5), in which the chamber 26 is pressurized. That is, any inflation of the cylinder 20 from the deflated state results in the external wall 24 being in tension. When the fluid within the chamber 26 is allowed to escape to depressurize the chamber 26, the external wall 24 will return to the deflated state shown in FIG. 4 and force the fluid out of the chamber 26.

When in the deflated state, the corrugations 22 within the wall 24 have first and second interior surfaces 30 and 32 that are displaced from each other by a distance D measured in the radial direction, as shown in FIG. 4. The distance D, or depth of the corrugations 22, is determined by the radial length of the sides 34 of the corrugations 22.

As the cylinder 20 expands radially in response to an increase in pressure within the chamber 26, the cylinder 20 reaches an inflated state that is illustrated in the cross-sectional view of FIG. 5. During the expansion, the corrugations 22 collapse resulting in a reduction to the distance D to the distance D'. The distance D' is dependent upon the pressure within the chamber 26, the material used to form the external wall 24, and other factors.

The amount of radial expansion the cylinder 20 undergoes as a result of the collapse of the corrugations 22 depends on the number of corrugations 22 and the change in the distance D (i.e., D-D') from the deflated to the inflated state. The more corrugations 22 in the cylinder 20, the greater the radial expansion that the cylinder 20 can undergo. The greater the change in the distance D, the greater the radial expansion that cylinder 20 can undergo.

In accordance with one embodiment, a portion 36 (indicated in phantom) in the corners of the corrugations 22 is removed or made more thin than the surrounding material to facilitate easier collapsing of the corrugations 22 and an increase in the change of the distance D during expansion of the cylinder 20 and, thus, an increase in the diameter of the inflated state of the cylinder 20.

In one embodiment, the external wall 24 of the cylinder is formed sufficiently thick to minimize the stretching of the wall beyond the collapse of the corrugations 22 under normal operating pressures.

In accordance with another embodiment, the external wall 24 of the cylinder is formed sufficiently thin to allow for radial expansion of the cylinder 20 beyond that due to the collapse of the corrugations 22 as a result of the stretching of the external wall. Thus, this embodiment of the cylinder 20 comprises a combination of the method of expansion of the conventional cylinder 20 along with that due to the corrugations 22.

Each of the embodiments of cylinder 20 discussed above facilitate providing an inflatable cylinder 20 having a smaller deflated state than prior art polyurethane or related cylinders. Furthermore, the embodiments of cylinder 20 of the present invention can provide a greater range of radial expansion over the polyurethane and related cylinders of the prior art. As a result, the cylinder 20 can have a smaller deflated diameter while providing an inflated diameter that is as large or a larger than related prior art cylinders. Thus, advantages of embodiments of the cylinder 20 over the related prior art cylinder 10 include, for example: easier installation into the corpora cavernosa of the patient, smaller flaccid diameter resulting in greater comfort to the patient, and a larger inflated diameter.

Additionally, the corrugations 22 help to soften the sharpness of bends made to the cylinder 20 when in the deflated or flaccid state. In general, when a bend in the cylinder 20 occurs there are four thicknesses of material at the bend, resulting in a larger bend radius. The larger bend radius produces a rounder, less sharp corner and results in greater comfort to the patient.

Another embodiment of the invention includes an inflatable penile prosthesis that includes embodiments of the cylinder 20 described above. Yet another embodiment of the invention relates to a method of inflating or expanding the cylinder 20.

Although the present invention has been described with reference to preferred embodiments, workers skilled in the art will recognize that changes may be made in form and detail without departing from the spirit and scope of the invention.

What is claimed is:

1. An inflatable penile prosthesis cylinder comprising:

an external wall defining a pressure chamber, the pressure chamber having an inflated state and a deflated state; and a plurality of corrugations formed in the external wall, the corrugations extending along a longitudinal axis of the cylinder, each corrugation comprising:

first and second circumferential walls extending along a circumference of the cylinder;

a first side wall extending from the first circumferential wall and along a radial direction from the longitudinal axis; and a second side wall opposite the first side wall, the second side wall extending from the first circumferential wall to the second circumferential wall and along the radial direction;

wherein:

the corrugations each have a depth corresponding to a distance the first and second circumferential walls are displaced from each other in the radial direction; and the depth of the corrugations when the cylinder is in the deflated state is greater than the depth of corrugations when the cylinder is in the inflated state.

2. The cylinder of claim 1, wherein the external wall is formed of polyurethane.

3. The cylinder of claim 1, wherein the diameter of the cylinder in the inflated state is greater than the diameter of the cylinder in the deflated state.

4. The cylinder of claim 1, wherein the deflated state is a quiescent state of the cylinder.

5. The cylinder of claim 1, wherein the external wall of the cylinder is placed in tension when the cylinder is in the inflated state.

6. A method comprising:

providing a penile prosthesis cylinder comprising:

an external wall defining a pressure chamber; and a plurality of corrugations formed in the external wall, the corrugations extending along a longitudinal axis of the cylinder, each corrugation comprising:

first and second circumferential walls extending along a circumference of the cylinder;

a first side wall extending from the first circumferential wall and along a radial direction from the longitudinal axis; and a second side wall opposite the first side wall, the second side wall extending from the first circumferential wall to the second circumferential wall and along the radial direction;

placing the penile prosthesis cylinder in a deflated state, in which the first and second circumferential walls are displaced from each other a distance D measured in a radial direction;

increasing the pressure within the pressure chamber; and inflating the penile prosthesis in the radial direction responsive to the increasing the pressure, wherein the distance D is reduced to a distance D' thereby increasing the circumference and diameter of the cylinder.

* * * * *